United States Patent [19]

Partanen et al.

[11] Patent Number: 5,063,024
[45] Date of Patent: Nov. 5, 1991

[54] METHOD AND APPARATUS FOR IMMUNOLOGICAL DETERMINATIONS

[75] Inventors: Paul Partanen; Helena Seppänen, both of Helsinki; Hannu Harjunmaa, Espoo, all of Finland

[73] Assignee: Labsystems OY, Helsinki, Finland

[21] Appl. No.: 377,538

[22] Filed: Jul. 10, 1989

Related U.S. Application Data

[63] Continuation of Ser. No. 53,859, May 13, 1987, abandoned.

[51] Int. Cl.$^5$ .................................... G01N 21/13
[52] U.S. Cl. .................................... 422/65; 356/246; 436/518; 436/531; 436/808; 436/809
[58] Field of Search ............... 436/807, 808, 531, 518; 356/246; 422/65, 73

[56] References Cited

U.S. PATENT DOCUMENTS 3,556,731  9/1973  Martin .................................... 422/65
4,236,825  12/1980  Gilford et al. .................... 422/63 X Primary Examiner—Robert J. Warden
Assistant Examiner—Lyle A. Alexander
Attorney, Agent, or Firm—Hopgood, Calimafde, Kalil, Blaustein & Judlowe

[57] ABSTRACT

The invention concerns an immunological assay system, wherein the inner face of the cuvettes is used as the solid phase. The equipment includes a displaceable carriage (8) for the cuvette set as well as, above the carriage, a dosage head (9), to which the liquid dosimeter (11) and the measurement device (19) are attached. All the operations take place automatically.

7 Claims, 3 Drawing Sheets

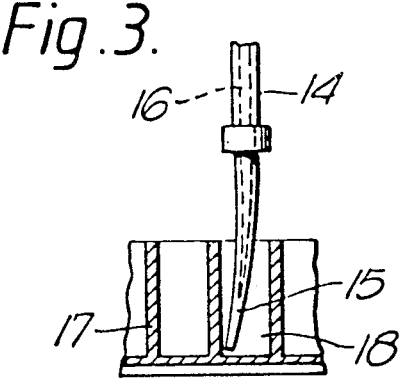
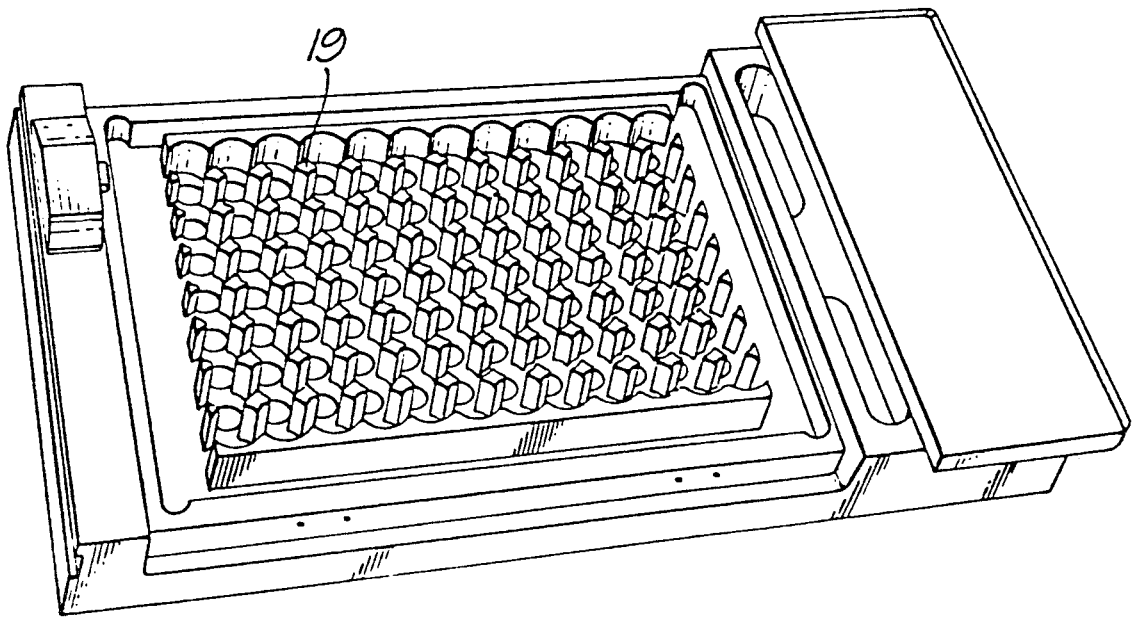

METHOD AND APPARATUS FOR IMMUNOLOGICAL DETERMINATIONS

BACKGROUND OF THE INVENTION

The present invention concerns an automatic immunoassay system, in which the inner face of the reaction vessel is used as the solid phase. The method of the invention may be used generally for photometric, fluorometric, phosphorimetric, or radiological immunoassays.

In order to determine an antibody (or antigen) present in a sample, so-called heterogeneous immunoassay methods are used, wherein the antibody (or antigen) and an antibody (or antigen) labelled with a tracer are allowed to be immobilized on an antigen (or antibody, respectively) in advance placed on a solid face. In these methods, the solid face, on which the immunological reaction has taken place, and the reaction solution are separated from each other before the signal of the tracer is measured from the solid face, in order that the excess tracer present in the reaction solution should not cover the signal in the antibody (or antigen) immobilized on the solid phase. The signal concerned may be, for example, radioactivity (RIA), fluorescence activity (FIA), or enzyme activity (EIA). In all of these methods, the solid phase must be washed carefully before the measurement.

The methods in use at present always include steps that must be performed manually; at least the washing step, for whose automation no means have been found that operate reliably in practice.

In automatized methods, attempts must be made to use sets of reaction and measurement cuvettes consisting of several sample vessels. As a rule, the reactions must be carried out at a precisely determined temperature. For the control of the temperature, incubators have been used, which comprise a heatable piece and therein a cuvette-shaped recess of its own for each cuvette in the cuvette set. This solution is, however, not satisfactory, for in this way it is difficult to make the temperatures in the different cuvettes to remain sufficiently precise at the desired level. For this reason, although the use of large cuvette sets may be desirable in these automated methods, these methods are limited to using smaller cuvette sets.

SUMMARY OF THE INVENTION

The object of the present invention is above all to provide a fully automatic heterogeneous logical assay system. A particular object is to provide a system in which the heating and washing steps also take place automatically and reliably even when large cuvette sets are used.

The apparatus now invented comprises: a cuvette-set carriage displaceable in the horizontal plane; a dosage head displaceable in the horizontal plane above the said carriage; a single-tip liquid dosimeter attached to the dosage head, which said dosimeter is provided with a tip that can be lowered to the bottom of the cuvette placed underneath; a dosage equipment for passing the desired liquid into the cuvette and for removing the solution placed in the cuvette out of the cuvette through the tip; as well as a measurement device attached to the dosage head.

A preferred embodiment of the invention will be illustrated in more detail by means of the attached drawings.

BRIEF DESCRIPTION OF THE DRAWINGS

FIG. 3 shows the tip of the liquid dosimeter lowered to the bottom of a cuvette.
FIG. 4 shows the thermostated incubator of the equipment.

DETAILED DESCRIPTION OF THE PREFERRED EMBODIMENT

Figure 1:
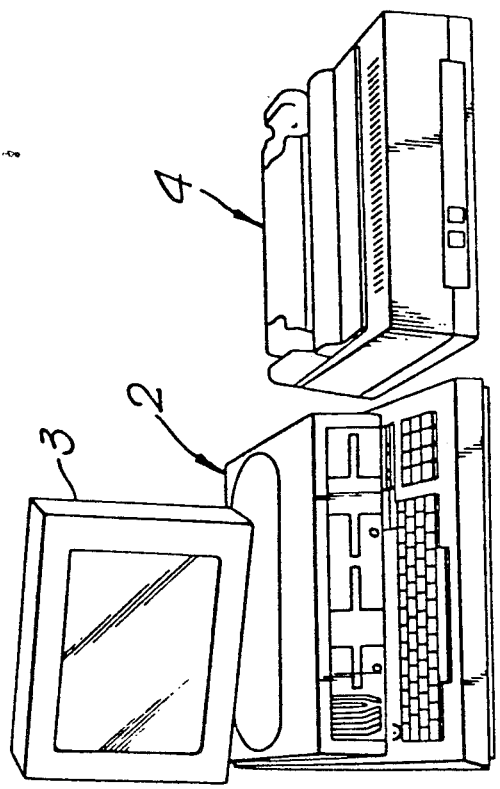
FIG. 1 is an overall illustration of the whole system of the present invention.
Figure 1:
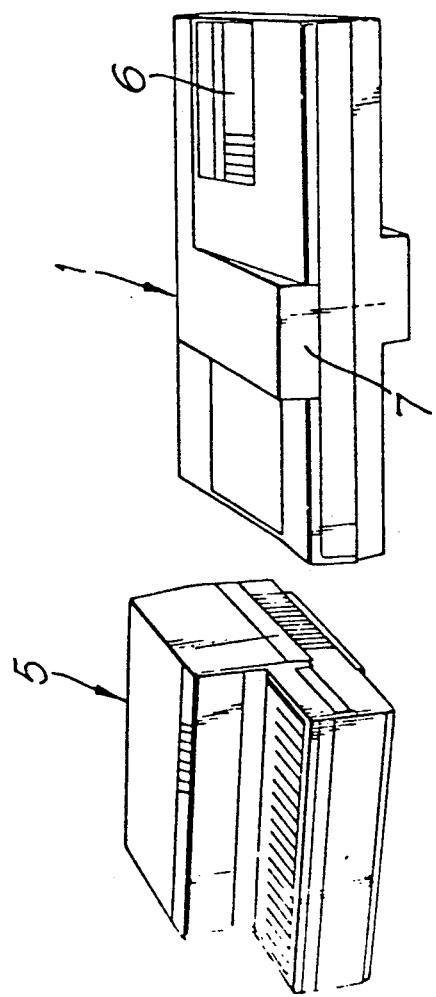
Figure 2:
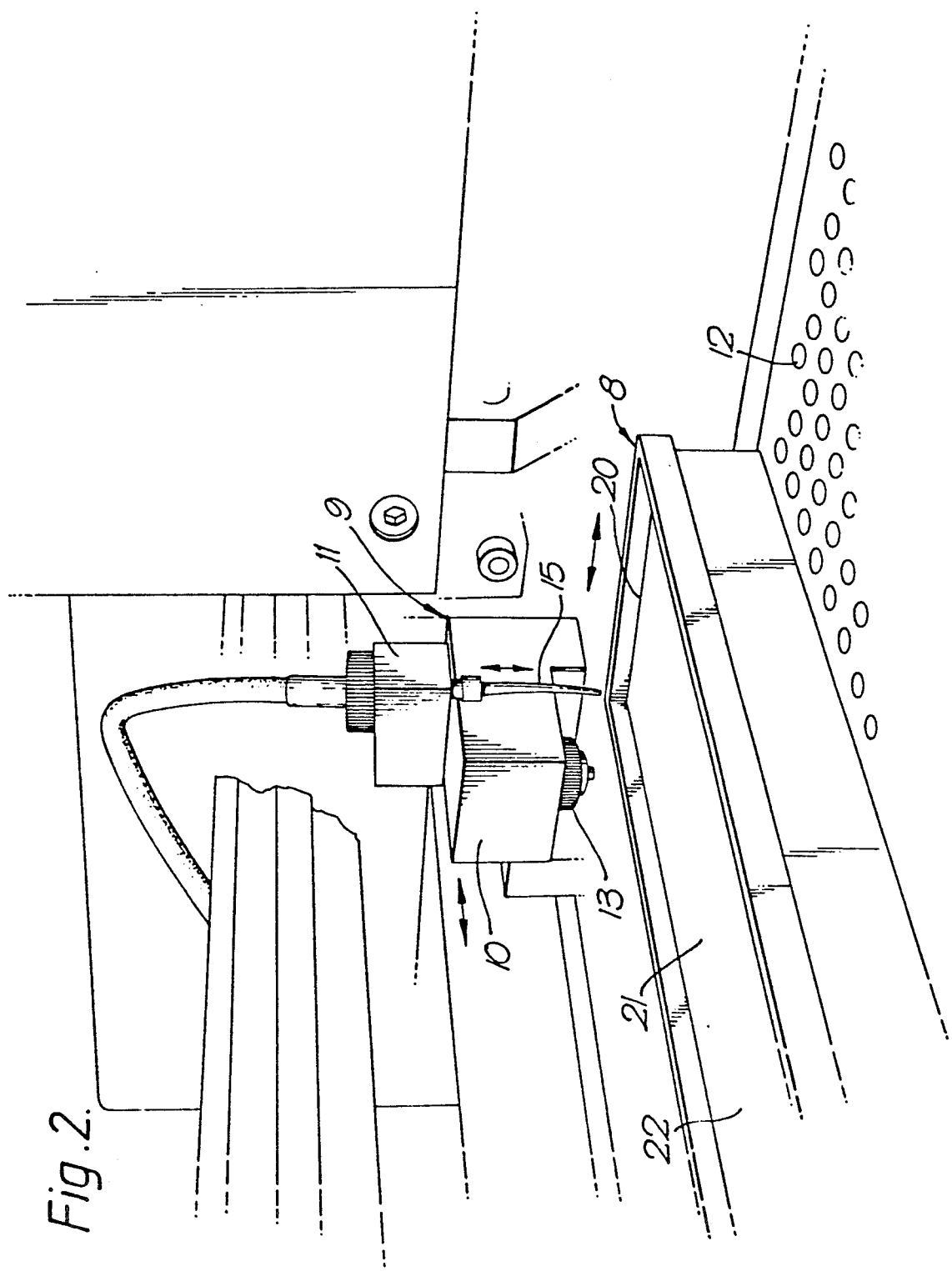
FIG. 2 is a partial view of the inside of the analyzer.

The main components of the equipment are an analyzer 1, a computer 2 with display terminal 3, and a printer 4. It is also possible to connect other control or data transfer and storage apparatuses 5 to the system. The analyzer has also an operating and output panel 6 of its own. The cover 7 of the analyzer is openable. The sample-cuvette set is placed on a mobile carriage 8. The path of movement of the carriage is rectilinear, denoted by the arrow shown at the end of the carriage. Above the carriage 8, there is a dosage head 9 displaceable along a path perpendicular to the path of movement of the carriage, to which said dosage head a photometer 10 and a liquid dosimeter 11 are attached. The direction of movement of the dosage head 9 is denoted with an arrow at the side of the head.

The measurement is carried out by passing a beam of light from below through the hole 12 through the bottom of the sample cuvette so as to be detected via the measurement tip 13 of the photometer 10.

In the liquid dosimeter 11 there is a main duct 14 connected to a tubing pump as well as a side duct 16 connected to a piston pump and opening into the said main duct (FIG. 3). The tip 15 of the liquid dosimeter can be lowered to the bottom of the cuvette placed underneath.

The tip 15 of the liquid dosimeter 11 is made of a resilient material and is preferably curved (FIG. 3). When the curved tip 15 is lowered to the bottom of a cuvette 18 in the cuvette set 17, the mouth of the tip becomes positioned in the corner of the cuvette 18. In this way it is possible to suck the liquid out of the cuvette 18 as completely as possible.

In the analyzer, a cuvette set 17 for vertical measurement is used, which comprises a number of cylindrical measurement cuvettes 18 provided with transparent bottoms, which said cuvettes are interconnected at their top edges by means of a support plate so as to make a rectangular matrix. Antigen of the antibody to be determined has been attached to the inner walls of the cuvettes 18, in particular to their bottoms, in advance. The carriage 8 is provided with holes pervious to light facing the cuvettes 18.

The carriage 8 is provided with a thermostated incubator, in which the cuvette set is placed. In the incubator, there are heating pins which become positioned between the cuvettes 18. The said pins 19 have a square section, whose sides are curved inwards following the walls of the cuvettes 18, so that a little gap remains between the pins 19 and the cuvettes (FIG. 4). In this way, air can circulate freely between the cuvettes, and the temperature in all the cuvettes remains as closely at the desired level as possible.

The carriage 8 has a location area 20 provided for the cuvette set 17, and so also a location area 21 for the sample vessels as well as a location area 22 for the necessary reagent and liquid-removal vessels.

The equipment operates as follows:

The cover 7 of the analyzer is opened, and the samples, such as serum samples, are placed in the location 21 provided for them, and the cuvette set 17 in the location 20 provided for it. The cover 7 is closed, and the desired program is started. The liquid dosimeter 11 fetches and dilutes each sample into its own cuvette 18 as well as fetches and measures the labelled antibody as well as any other reagents that may be required into each cuvette. The samples are incubated for the desired period of time, whereby the immunological reaction takes place.

Now the liquid dosimeter 11 sucks the reaction solutions from all of the cuvettes 18 alternatingly into the main duct 14 and evacuates them into the vessel provided for them, while at the same time rinsing the duct. Now washing liquid is measured alternatingly into all of the cuvettes out of the main duct 14, whereupon the cuvettes are again emptied in the way described above. Finally, the amount of labelled antibody immobilized on the bottom of each cuvette is measured from the said bottoms, and the results of the assays are produced as an output in the desired way.

The solution is removed from the cuvette so that the tip 15 is pushed onto the bottom of the cuvette 18, and when liquid is being sucked off, the curved tip 15 is shifted to against the corner of the cuvette. In this way the tip 15 is always placed precisely in the corner of the cuvette 18, and the solution can be removed as completely as possible.

The washing liquid is measured into the cuvette 18 so that the liquid jet does not detach the reacted antibody, but, however, detaches any excess labelled antibody as well as any other impurities into the solution.

Above, a preferred photometric embodiment has been described. The arrangement may, however, also be applied to fluorometric or radiological measurement. The equipment may also differ from that described above in other respects as regards its details. For example, it may have a separate incubation station, into which the carriage is driven. The dosage head may, of course, also be used during incubation, and so may the photometer.

In an advantageous embodiment, several different assay sequences are carried out at the same time.

What is claimed is:

1. An immunological assay equipment comprising:
   a carriage (8) displaceable along a rectilinear path in a horizontal plane,
      said carriage including a location area (20) for supporting a cuvette set (17) comprising a plurality of spaced cuvettes (18) of cylindrical shape,
      said cuvette set (17) with its plurality of cuvettes (18) constituting a rectangular matrix in which the cuvettes are joined by means of a plate to provide said cuvettes in predetermined spaced apart relationship,
      said carriage also including a location area (21) adjacent to area (20) for supporting samples,
      said location area (20) including a thermostated incubator having spaced heating pins (19) through which heat is conducted, said pin (19) being positioned to enter and occupy spaces between cuvettes (18) when said cuvette set is positioned in said incubator,
      each of said heating pins (19) having a quadrangular shape with its sidewalls concaved to conform to the cylindrical walls of the cuvettes so that air can circulate freely between the cuvettes,
      each of said cuvettes (18) having an antigen of an antibody or an antibody of an antigen immobilized onto inner faces of said cuvettes (18) of said cuvette set (7),
   a dosage head (9) displaceable along said carriage (8) in a horizontal plane,
      said displacement being along a rectilinear path perpendicular to said carriage path,
   a single-tip liquid dosimeter (11) attached to dosage head (9) having a tip capable of being lowered onto the bottom of said cuvette (18) disposed beneath dosimeter (11),
   a dosage equipment for passing liquid into cuvette (18) and removing solution therefrom via tip (15),
   a measuring device (10) attached to dosage head (9) for measuring signals given by a trace agent adhering to inner faces of cuvettes (18),
      said assay equipment being fully automated so that cuvettes (18) placed therein may be dosed, incubated and their contents accordingly analyzed.

2. The assay equipment as in claim 1, wherein the diameter of the location of the cylindrical cuvette formed by said heating pins is slightly larger than the diameter for cuvette (18).

3. The assay equipment as in claim 1, wherein tip (15) of liquid dosimeter (11) is curved.

4. The assay equipment as in claim 1, wherein tip (15) is resilient.

5. The assay equipment as in claim 1, wherein the tip (15) of liquid dosimeter (11) is comprised of a main duct (14) and a side duct (16) opening into the main duct.

6. The assay equipment as in claim 1, wherein said measuring device includes:
   means for passing a beam of light through the bottom of cuvette (18) from below; and
   a photometer (10) having a measuring tip (13) positioned to detect said beam after said beam passes through said cuvette.

7. A method for assaying either an antigen of an antibody or an antibody of an antigen which comprises:
   providing a cuvette set (17) in the form of a rectangular matrix comprising a spaced arrangement of cylindrically shaped cuvettes (18),
   providing a thermostated incubator having spaced heating pins (19) of quadrangular shape through which heat is conducted positioned to enter and occupy spaces between said cylindrical cuvettes,
      each sidewall of said quadrangular pin being concaved to conform to the cylindrical shape of the cuvette so that air can circulate freely between the cuvettes,
   applying to the inner faces of said cuvettes (18) either an antigen of an antibody or an antibody of an antigen to be measured,
      said applied antigen or antibody being immobilized,
   placing said cuvette set 17 on said thermostated incubator on carriage (8) displaceable in a horizontal plane,
   placing sample vessels containing samples to be measured and reagent vessels on said carriage (8), transferring via single-tip (15) of liquid dosimeter (11) portions of liquid from sample vessels and reagent vessels by lowering tip (15) to the bottom of each of cuvettes (18), allowing an immunological reaction to take place at a predetermined thermostated temperature in said cuvette (18) whereby a tracer agent adheres to the inner faces of said cuvettes (18), removing said solutions from each of cuvette (18) by means of tip (15), washing said cuvettes (18) with a washing solution, and then measuring the signal given off by a tracer agent adhering to the inner faces of cuvettes (18).

* * * * *

UNITED STATES PATENT AND TRADEMARK OFFICE
CERTIFICATE OF CORRECTION

PATENT NO. : 5,063,024

DATED : November 5, 1991

INVENTOR(S) : Paul Partanen et al.

It is certified that error appears in the above-identified patent and that said Letters Patent is hereby corrected as shown below:

On title page, insert item;

```
--[30] Foreign Application Priority Data
   Oct. 7, 1985  Finland -----853,895--.
```

Signed and Sealed this

Ninth Day of March, 1993

*Attest:*

STEPHEN G. KUNIN

*Attesting Officer*  *Acting Commissioner of Patents and Trademarks*